United States Patent
Dubielczyk et al.

(10) Patent No.: US 10,602,962 B2
(45) Date of Patent: Mar. 31, 2020

(54) SYSTEM AND METHOD FOR DETERMINING VITAL SIGN INFORMATION OF A SUBJECT

(71) Applicant: KONINKLIJKE PHILIPS N.V., Eindhoven (NL)

(72) Inventors: Alexander Dubielczyk, Gaertringen (DE); Christian Michael Epping, Goeppingen (DE); Rolf Neumann, Calw (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1241 days.

(21) Appl. No.: 14/521,944

(22) Filed: Oct. 23, 2014

(65) Prior Publication Data

US 2015/0126872 A1    May 7, 2015

Related U.S. Application Data

(60) Provisional application No. 61/898,554, filed on Nov. 1, 2013.

(30) Foreign Application Priority Data

Nov. 1, 2013  (EP) ..................................... 13191299

(51) Int. Cl.
*A61B 5/087* (2006.01)
*A61B 90/00* (2016.01)
(Continued)

(52) U.S. Cl.
CPC .......... *A61B 5/0873* (2013.01); *A61B 5/0075* (2013.01); *A61B 5/0077* (2013.01);
(Continued)

(58) Field of Classification Search
CPC ..... A61B 5/0075; A61B 5/0077; A61B 5/087; A61B 5/0876; A61B 5/091; A61B 5/1127;
(Continued)

(56) References Cited

U.S. PATENT DOCUMENTS 4,945,919 A * 8/1990 Hattori ..................... A61B 5/01
                                                                374/162
5,704,367 A   1/1998 Ishikawa et al.
(Continued)

FOREIGN PATENT DOCUMENTS

DE   102012104419 B3   4/2013
WO   2011157873 A1    12/2011
(Continued)

OTHER PUBLICATIONS

Ristic et al. ("Flow visualization technique in wind tunnels", Scientific Technical Review, vol. LVII, No. 1, pp. 39-50, 2007.*
(Continued)

*Primary Examiner* — Carolyn A Pehlke
*Assistant Examiner* — Marjan Saboktakin (57) ABSTRACT

Vital sign information of a subject is determined using a marker for application to the subject. The marker is configured to change an optical property due to a mechanical manipulation of the marker caused by a physiological process of the subject. The change in the optical property is detected and analyzed to determine vital sign information of the subject.

19 Claims, 3 Drawing Sheets

(51) Int. Cl.
*A61B 5/11* (2006.01)
*A61B 5/00* (2006.01)
*A61B 5/091* (2006.01)

(52) U.S. Cl.
CPC ............ *A61B 5/087* (2013.01); *A61B 5/0876* (2013.01); *A61B 5/091* (2013.01); *A61B 5/1127* (2013.01); *A61B 5/682* (2013.01); *A61B 5/6819* (2013.01); *A61B 5/6833* (2013.01); *A61B 5/7278* (2013.01); *A61B 90/39* (2016.02); *A61B 5/1114* (2013.01); *A61B 2090/3945* (2016.02); *A61B 2090/3979* (2016.02); *A61B 2090/3991* (2016.02)

(58) Field of Classification Search
CPC ..... A61B 5/6819; A61B 5/682; A61B 5/6833; A61B 5/7278
See application file for complete search history.

(56) References Cited

U.S. PATENT DOCUMENTS

| | | | |
|---|---|---|---|
| 6,110,123 | A | 8/2000 | Ishihara et al. |
| 9,615,774 | B2 * | 4/2017 | Kobayashi ............ A61B 5/082 |
| 2003/0199780 | A1 * | 10/2003 | Page .................... A61B 5/0816 |
| | | | 600/538 |
| 2005/0106977 | A1 | 5/2005 | Coulston |
| 2007/0076935 | A1 * | 4/2007 | Jeung ...................... A61B 5/08 |
| | | | 382/128 |
| 2009/0141124 | A1 | 6/2009 | Liu et al. |
| 2009/0204100 | A1 | 8/2009 | Van Pieterson et al. |
| 2010/0249560 | A1 * | 9/2010 | Levinson ............... A61B 5/021 |
| | | | 600/364 |
| 2012/0052469 | A1 | 3/2012 | Sobel et al. |
| 2012/0289850 | A1 | 11/2012 | Xu et al. |
| 2013/0030257 | A1 * | 1/2013 | Nakata ................. A61B 5/0507 |
| | | | 600/301 |
| 2013/0079658 | A1 | 3/2013 | Cardoso et al. |
| 2014/0221847 | A1 | 8/2014 | Dubielczyk et al. |
| 2014/0243648 | A1 | 8/2014 | Dubielczyk |

FOREIGN PATENT DOCUMENTS

| | | |
|---|---|---|
| WO | 2012140531 | 10/2012 |
| WO | 2013186696 A1 | 12/2013 |

OTHER PUBLICATIONS

Corten, et al., "Flow Separation on Wind Turbine Blades", 1968, XP001164271.
Covidien; NellcorTM, Adult/Pediatric Calorimetric CO2 Detector; www.Covidien.com downloaded Oct. 21, 2014.
Dansby-Sparks, R. N., et al.; Fluorescent-Dye-Doped Sol-Gel Sensor for Highly Sensitive Carbon Dioxide Gas Detection below Atmospheric Concentrations; 2010; Anal. Chem.; 82:593-600.
Frigola, M., et al.; Vision Based Respiratory Monitoring System; 2002; Proc. 10th Mediterranean Conf. on Control and Automation; 5 pages.
Malins, C., et al.; Dye-doped organically modified silica glass for fluorescence based carbon dioxide gas detection; 1998; Analyst; 123:2373-2376.
Murthy, R., et al.; Noncontact Measurement of Breathing Function; 2006; IEEE Engineering in Medicine and Biology Magazine; pp. 57-67.
Segawa, H., et al.; Sensitivity of fiber-optic carbon dioxide sensors utilizing indicator dye; 2003; Sensors and Actuators B: Chemical; 94(3)276-281.
Topal, S. Z., et al.; A new absorption based CO2 sensor based on Schiff based doped ethyl cellulose; 2012; Turk. J. Chem.; 36:503-514.
Verkruysse, W., et al.; Remote plethysmographic imaging using ambient light; 2008; Opt. Express; 16(26) 21434-21445.
Wolfbeis, O. S., et al.; Fiber-Optic Fluorosensor for Oxygen and Carbon Dioxide; 1988; Anal. Chem.; 60:2028-2030.
Ristic, S.; Flow Visualisation Techniques in Wind Tunnels Part I-Non optical Methods; 2007; Scientific Technical Review; 1.VII(1)39-50.

* cited by examiner

SYSTEM AND METHOD FOR DETERMINING VITAL SIGN INFORMATION OF A SUBJECT

CROSS REFERENCE TO RELATED APPLICATIONS

This application claims the benefit of U.S. provisional application Ser. No. 61/898,554 filed Nov. 1, 2013 and EP provisional application serial no. 13191299 filed Nov. 1, 2013, both of which are incorporated herein by reference.

FIELD OF THE INVENTION

The present invention relates to a system and method for determining vital sign information of a subject, in particular to optical measurement for remotely determining vital signs of an observed subject.

BACKGROUND OF THE INVENTION

Vital signs of a subject, for example the heart rate (HR), the respiration rate (RR) or the body temperature serve as indicators of the current health status of a person and as powerful predictors of serious medical events. For this reason, vital signs are extensively monitored in in-patient and out-patient care settings, at home or in further health, leisure and fitness settings.

US 2009/0204100 A1 discloses a body cover comprising a temperature sensing element. The temperature sensing element senses the temperature of proximate skin and converts the locally sensed temperature into a visual and/or electrical signal. The body cover may include a local display for converting electrical signals that are output by temperature sensing elements into a visual signal such that a wearer or a camera can read the state of the skin from the body cover.

U.S. Pat. No. 4,945,919 discloses a rhinological diagnostic device comprising a thermochromic liquid crystal layer for displaying a temperature distribution of expired air in a thermochromic pattern for diagnosing an abnormality in the nasal cavity.

US 2012/0289850 A1 discloses monitoring respiration of a subject with a thermal imaging system set to a temperature range of a facial region. A thermal camera operating in the infrared wavelength range of 7,500 nm to 14,000 nm captures a thermal image video sequence. Temperatures of extremities of the head and face are used to locate facial features in the captured thermal images, i.e., nose and mouth, which are associated with respiration. Since the temperature of the exhaled air typically has a higher temperature than the inhaled air, a temporal variation of the nose and mouth region can be evaluated to determine the respiration rate. In an alternative embodiment, the respiration rate is determined by the motion of the nostrils, lips or chest.

US 2012/0052469 A1 discloses a nasal flow controller device. An air flow during sniffing-in cools a region about the nose and air-flow during sniffing out warms a region about the nose. A pad can be attached to the subject's nose which responds sufficiently fast to temperature variations. A camera again senses the temperature variations.

A disadvantage of such systems is that a thermal measurement only works if there is a significant temperature difference between environmental temperature and exhaled air temperature. A further disadvantage is that thermal cameras are expensive. Furthermore, additional measurement modalities are needed to measure additional vital signs like the heart rate or oxygen saturation in parallel.

As an alternative to thermal imaging, U.S. Pat. No. 6,110,123 A discloses motion-based respiration measurement. A prerequisite for this technique is that respiration correlated movements must be visible for the camera system. Preferentially, a movement of the chest is observed since respiratory movements are usually not visible in the face. However, for example in a hospital setting where the patient is lying in bed and covered with a blanket, only a very limited respiratory movement can be observed. Furthermore, a chest movement does not guarantee a gas flow into the lungs. Furthermore, a motion-based respiration measurement is susceptible to motion artifacts.

SUMMARY OF THE INVENTION

It is an object of the present invention to provide an improved system and method for unobtrusively and economically determining vital sign information of a subject. It would be particularly advantageous to provide a system and method that enhance the functionality of a low-cost device for determining vital sign information.

In a first aspect of the present invention a system for determining vital sign information of a subject is presented that comprises
a marker applied to the subject, wherein the marker is configured to change an optical property due to a mechanical manipulation of the marker caused by a physiological process of the subject,
a detection unit that detects radiation from the marker, and
an analysis unit that determines the vital sign information of the subject from the detected radiation.

In a further aspect of the present invention a marker for use in the aforementioned system is presented, wherein the marker is configured for application to the subject, and wherein the marker is configured to change an optical property due to a mechanical manipulation of the marker caused by a physiological process of the subject.

In a further aspect of the present invention, a method for determining vital sign information of the subject is presented that comprises the steps of
detecting radiation from a marker, wherein the marker is applied to the subject, and wherein the marker is configured to change an optical property due to a mechanical manipulation of the merker caused by a physiological process of the subject, and
determining the vital sign information of the subject from the detected radiation.

Preferred embodiments of the invention are defined in the dependent claims. It shall be understood that the claimed marker and method have similar and/or identical preferred embodiments as the claimed system and as defined in the dependent claims.

The term 'vital sign' as used in the context of the present invention refers to a physiological parameter of the subject and derivative parameters. In particular, the term 'vital sign' comprises heart rate (HR) (sometimes also called pulse rate), heart rate variability (pulse rate variability), pulsatility strength, perfusion, perfusion indicator, perfusion variability, Traube Hering Mayer waves, respiratory rate (RR), body temperature, blood pressure, a concentration of substance in blood and/or tissue and/or sweat, such as an oxygen saturation or a glucose level. In general, a 'vital sign' can be descriptive of an underlying physiological process such as cardiac pulses or a respiratory activity. A physiological signal descriptive of the underlying physiological process can be measured and evaluated.

The term 'vital sign information' as used in the context of the present invention comprises the one or more measured vital signs as defined above. Furthermore, the term 'vital sign information' comprises data referring to a physiological parameter, corresponding waveform traces or data referring to a physiological parameter over time that can serve for subsequent analysis.

A major drawback of existing measurement devices for determining vital signs is that they are tailored for a specific application such that a plurality of different devices is required to cover the desired vital signs. For example the thermal camera according to US 2012/0289850 A1 is used for determining the respiration rate, and an additional camera operating in a visible part of the spectrum is used for determining a heart rate by remote photo-plethysmography. Verkruysse et al., "*Remote plethysmographic imaging using ambient light*", Optics Express, 16 (26), 22 Dec. 2008, pp. 21434-21445 demonstrate that photo-plethysmographic signals can be measured remotely using ambient light and a conventional consumer level video camera. Different devices are needed, since the desired underlying physical quantities cannot be observed by one single device.

As a solution, the present invention is based on the idea that a marker is applied to the subject wherein the marker is configured to change an optical property in response to a physiological process of the subject. In other words, the marker is used to convert vital sign information, which is invisible itself to the measurement modality, to be detectable by that measurement modality.

For example, the marker is configured to change an optical property, such as a color or brightness, in response to a respiratory gas volume flow. A detection unit such as a low-cost CCD camera detects radiation received from the marker. In a next step, the analysis unit analyzes the detected radiation and determines the respiratory rate by evaluating a temporal change of the optical property of the marker.

As used herein, the term 'detection unit' refers to a device for detecting electromagnetic radiation. It is configured to detect radiation received from the marker. In a preferred embodiment, the detection unit is a camera with an image sensor such as a CCD or CMOS image sensor that comprises an array of light sensitive pixels. The output of the detection unit is referred to as radiation data. For example, the radiation data is a series of images over time, thus a video stream. The camera can be a monochrome or color camera. In an embodiment, the detection unit is a remote detection unit, wherein the detection unit is spatially separated from the observed subject. In an embodiment, the detection unit is configured to detect light in a spectral range of about 420 to 1100 nm.

In an embodiment, the marker is configured to change an optical property due to one of a mechanical, physical or chemical manipulation of the marker caused by a physiological process of the subject. As examples for a mechanical manipulation, the marker is configured to change an optical property in response to a gas volume flow due to respiration, or in response to stress introduced by a muscular activity or dilation of blood vessels. As an example of a physical manipulation, the marker is configured to change an optical property in response to a temperature change, for example induced by respiration. As an example of a chemical manipulation, the marker is configured to change an optical property in response to a gas concentration for example constituents of exhaled air like carbon dioxide or other reaction product, a chemical property of the skin surface, such as a pH value, humidity and the like.

In an embodiment, the changing optical property of the marker is a reflectivity and/or color. The term 'reflectivity' as used herein also refers to a reflection, in particular specular reflection, as well as brightness or absorption characteristics. The changing optical property also includes an apparent change of an optical property. For example, an orientation of a structural element of the marker may be altered in response to a physiological process. Thus, the color of the structural element of the marker does not actually change. However, the different orientation of the structural element of the marker provides the detection unit with a different optical impression.

In a further embodiment, the marker is a patch, in particular a patch for application to a skin of the subject. An advantage of this embodiment is that medical personnel is used in handling patches, such as band-aids, in everyday practice. Alternatively, the marker can be configured for direct application to the subject, in particular to the skin of the subject. For example the marker can be provided in form of a lipstick or unguent, cream or lotion. Further alternatively, the marker can be configured for application to a tubus or other medical equipment in proximity to the patient which is affected by a physiological process of the subject, such as a respiratory flow of air.

In an embodiment, the marker is configured for application to a nasal and/or oral region of the subject. The regio oralis is particularly well suited for application since it is affected by a respiratory flow of air and is seldom covered by a blanket. Further advantageously, a patch for fastening a tube for supplying the patient with oxygen can carry the marker in the supralabial region or in proximity to the philtrum.

In an embodiment, a surface of the marker comprises filaments protruding from said surface. Advantageously, the filament is a structural element that is configured to be moved by an airflow which causes a change in its optical appearance. For example, a surface of the marker comprises flexible filaments, in particular textile fibers that are configured to move in response to a mechanical manipulation such as a gas volume flow. For example, a marker comprising said filaments on the surface is attached to the supralabial region underneath the nose, above the upper lip of the subject. During inhalation, the filaments are affected by the gas volume flow and align in an upward direction, i.e., towards an airway, whereas during exhalation the filaments are arranged to move downwards, i.e., away from the airway. The marker can be configured to provide a different optical impression which depends on the orientation of the filaments.

In a further refinement, the filaments comprise a first surface having a first optical property and a second surface having a second optical property. For example, the first surface and the second surface can have different colors, be black and white, have different reflection or scattering properties. Preferably, the first and second surface provide a high contrast. In an alternative embodiment, the filaments have a first optical property and the surface of the marker from which the filaments are protruding from has a second optical property. Thus, depending on how much of the surface is visible to the detection unit, information about an orientation of the filaments can be inferred. It should be noted that it is not mandatory to know the exact orientation of the filaments since it can be sufficient to analyze a relative change in the detected radiation from the marker. However, preferably the first optical property and the second optical property provide a high contrast.

In an embodiment, the detection unit comprises an image sensor or camera. Advantageously, the image sensor is a standard CCD or CMOS image sensor that is available at low cost. This is a significant advantage compared to the solution proposed in US 2012/0289850 A1 where an expensive thermal camera operating in the mid infrared (IR) or long IR wavelength range from 7500 nm to 14000 nm is employed.

In a further embodiment, the detection unit is configured to detect non-visible radiation, in particular near infrared (IR) and/or near ultraviolet (UV). An advantage of this embodiment is that vital sign measurements can be performed in darkness, thus without disturbing the patient at night. Furthermore, it is possible to use a marker wherein the color of the marker corresponds to the color of the skin of the subject in the visible range. Thus, the marker is configured to change an optical property in the non-visible part of the spectrum. Thereby, an aesthetic appearance is improved. Near infrared can be defined as a wavelength range of 750 nm to 1400 nm. Near ultra violet can be defined as a wavelength range of 300 nm to 400 nm. Visible light can be defined as a wavelength range from 400 nm to 750 nm. The detection unit can be configured to detect near infrared and/or near ultraviolet light in addition to visible light or in alternative to visible light.

In an embodiment, the detection unit is configured to detect radiation in a spectral range, wherein the spectral range lies in a wavelength range between 300 nm and 1400 nm, preferably between 400 nm and 1100 nm. The spectral range can be a part of the wavelength range. A typical spectral range for a CCD sensor as an exemplary detection unit is between 420 nm and 1100 nm. Alternatively, the spectral range covers one or more separate or overlapping sub-ranges, for example in the red, green and blue part of the visible spectrum.

Optionally, the system for determining vital sign information of the subject further comprises a light source, for example a visible light source, near IR or near UV light source.

In an embodiment, the analysis unit is configured to evaluate the detected radiation over time. Thus, an absolute value does not have to be known. For example, the respiratory rate can be determined by evaluating a time series of the measured radiation data. Advantageously, long-term monitoring of a subject enables a comparison of measurement values of the subject at different points in time, thus a self-referencing system. Thereby, an improving or deteriorating condition can be determined. Furthermore, aging of the marker can be considered. For example, a marker that changes its optical property based on a mechanical manipulation or chemical manipulation may degrade over time such that its ability to change its optical property wears off. Optionally, this aging of the marker can also be considered, for example by applying a correction function in the analysis unit.

In a further refinement, the marker is configured to change an optical property in response to a respiration of the subject, and wherein the analysis unit is configured to derive information about the tidal volume. In addition to evaluating absolute values, a relative change can be evaluated for example for indicating a decreasing tidal volume.

In another embodiment, the marker is further configured to visualize a physiological property of the subject by the optical property. For example, an absolute value, such as a temperature or a concentration of a chemical substance, can be indicated by the optical property of the marker, wherein the optical property changes in response to a physiological process of the subject. Optionally, the marker further comprises a reference area on the marker as a reference for determining the absolute value. This is particularly advantageous since the appearance of the optical property to the detection unit may depend upon and change with different lighting conditions.

In a further embodiment, the marker comprises one or more additional optical features for detection by the detection unit of a group of features comprising an optical feature for tracking the marker, for reference, for measurement at night and for information coding. For example, the marker can comprise a bar code or QR-code that comprises information about the patient that is to be measured and/or information about the measurement procedure. Furthermore, the marker can comprise distinct optical features which enable tracking of the marker in the detected radiation. Optionally, the system further comprises an image processing unit for identifying the marker in the detected radiation.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
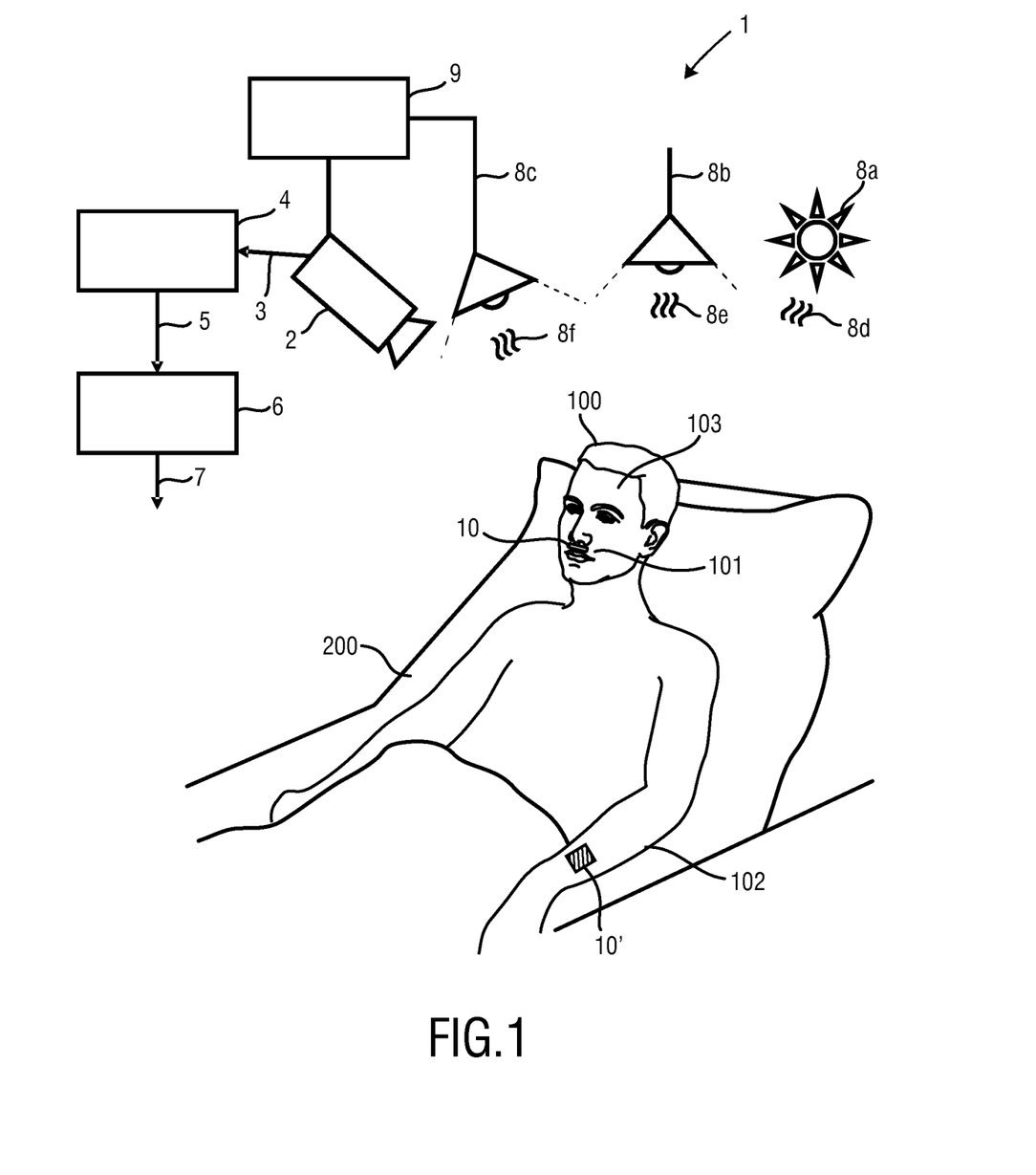
FIG. 1 shows an exemplary embodiment of a system for determining vital sign information of a subject according to the present invention.

FIG. 1 shows an exemplary embodiment of a system 1 for determining vital sign information 7 of a subject 100 according to an aspect of the present invention. The system 1 comprises a marker 10 for application to the subject 100, a detection unit 2 and an analysis unit 6, for example an electronic processor, as the basic components. In this example, the system 1 for determining vital sign information 7 of the subject 100 is employed in a clinical setting, where the subject 100 lies in bed 200.

The marker 10 is configured to change an optical property in response to a physiological process of the subject 100. In this example, the detection unit 2 is connected to an optional image processing unit 4. The detection unit 2 provides radiation data 3 that represents the detected radiation to the image processing unit 4 in form of a video stream. The image processing unit 4 identifies the marker 10 in the radiation data 3. The image processing unit 4 in turn is connected to the analysis unit 6. The image processing unit 4 provides pre-processed radiation data 5 to the analysis unit 6. The pre-processed radiation data 5 in this example comprises information about which region of the images of the video stream of the radiation data 3 depict the marker 10. The analysis unit 6 in turn determines the vital sign information 7 of the subject 100 from the detected radiation.

The image processing unit 4 for identifying the marker 10 can also be incorporated into the analysis unit 6. Alternatively, the radiation data 3 is directly provided to the analysis unit 6. In this case, the marker 10 can either be determined by manually selecting the marker 10 in the images of the video stream. Alternatively, the subject 100 with the marker 10 has to be located in a predetermined position within the field of view of the detection unit 2 such that the marker 10 is located at a predetermined position. However, an automated identification of the marker 10 in the radiation data 3 by the image processing unit 4 is preferred. In the shown example, the marker 10 is directly applied to the bare skin of the nasal/oral region 101 of the subject 100. An alternative marker 10' is located at the left forearm 102 of the subject 100. The size and shape of the marker 10, 10' can be adapted depending on the anatomic location.

The system 1 for determining vital sign information 7 of the subject 100 can be further configured as a system for measuring vital signs by remote photo-plethysmography. Plethysmography historically refers to the measurement of volume changes of an organ or body part and in particular to the detection of volume changes due to a cardio-vascular pulse wave traveling through the body of the subject 100 with every heartbeat. Photo-plethysmography (PPG) is an optical measurement technique that evaluates a time-variant change of light reflectance or transmission of an area or volume of interest. For example, PPG for determining a heart rate is based on the principle that blood absorbs light more than surrounding tissue, so variations in blood volume with every heartbeat affect transmission or reflectance correspondingly. Every heartbeat causes small changes in the color of a face of the subject. These changes are not visible to the eye, but the detection unit 2 is configured to detect these "micro-blushes". The time-variant color change can be provided as a PPG waveform which is evaluated by the analysis unit 6 to measure the heart rate as the vital sign information 7.

Besides information about the heart rate, the PPG waveform can comprise information attributable to further physiological phenomena such as the respiration. By evaluating the transmissivity and/or reflectivity at different wavelengths (typically red and infrared as mentioned before), the blood oxygen saturation can be determined.

However, the measurement of a respiration rate based on a faint color change of skin of the subject 100, for example measured at the forehead 103 of the subject 100, requires a good signal-to-noise ratio. However, this is not always the case under all measurement conditions. As a solution, the prior art discloses using a thermal imager or alternatively evaluating body movements to determine a respiration rate. In contrast to the prior art, the present invention suggests to apply a marker to the subject, wherein the marker 10 is configured to change an optical property in response to a physiological process of the subject 100. Thereby, vital sign information gets detectable by a detection unit 2, in particular a low-cost standard CCD sensor. In this context, the detection unit 2 can also be referred to as a vital signs camera.

The scenery in FIG. 1 is illuminated by a source of radiation, such as sunlight 8a or an artificial light source 8b. The radiation source 8a, 8b directly or indirectly emits radiation 8d, 8e towards the subject 100. In addition, or in the alternative, the system 1 can also comprise an optional system light source 8c that emits light 8f towards the subject 100. The use of the system light source 8c is particularly beneficial if the ambient light sources 8a, 8b do not provide sufficient light or if the spectrum of the ambient light sources 8a, 8b does not provide sufficient power in a desired spectral region.

An optional control unit 9 is adapted to control the sensitivity of the detection unit 2 and/or to control the power of the system light source 8c. Because the dynamic range of detector or image sensor that is used as the detection unit 2 is limited, shutters and electronic offsets may have to be adjusted according to the lighting situation in the observed scene. The system light source 8c can be part of a control loop which sets an optimal operating point of the image sensor of the detection unit 2. Optimal in this context refers to an output signal without signal clipping, no saturation of individual detectors of the image sensor and a good signal-to-noise ratio at least for the detection area corresponding to the marker 10, 10'.

Advantageously, the detection unit 2 comprises a standard image sensor for detecting radiation from the scenery with the marker 10, 10'. In a preferred embodiment, the detection unit is an off-the-shelf camera operating in a wavelength region between 300 nm to 1400 nm, preferably between 420 nm and 1100 nm, preferably between 420 nm and 750 nm, preferably in the visible range. It should be noted that the wavelength region of the detection unit preferably includes at least some near ultraviolet (UV) light and/or some near infrared (IR) light wavelengths. The corresponding detection characteristics are commonly found in low-cost image sensors, in particular in commercially available CCD or CMOS image sensors, in particular Silicon-based image sensor. An image sensor as used herein does explicitly not refer to a thermal imager operating in the mid to long infrared wavelength range of 7,500 nm to 14,000 nm. Thus, the system 1 with the detection unit 2, the analysis unit 6 and the marker 10 can be provided at much lower cost.

In an embodiment, the system light source 8c is configured to emit non-visible radiation 8f, in particular near infrared and/or near ultraviolet light. Thereby, the subject 100 can be monitored at night or darkness in terms of the visible wavelength spectrum, without disturbing the subject 100. Optionally, the system light source 8c is configured to emit light with different spectral properties, for example red and infrared light or red and green light at the same and/or different times to enable a measurement of blood oxygen saturation, as for example disclosed by Wieringa et al. "*Contactless Multiple Wavelength Photo-Plethysmographic Imaging: A First Step Towards "SPO2 Camera" Technology*", Annals of Biomedical Engineering, vol. 33, No. 8, 2005, pp. 1034-1041.

Exemplary embodiments of markers are shown in and explained with reference to FIGS. 2 to 6. The marker 10 is configured to change an optical property in response to a physiological process of the subject 100.

Figure 2:
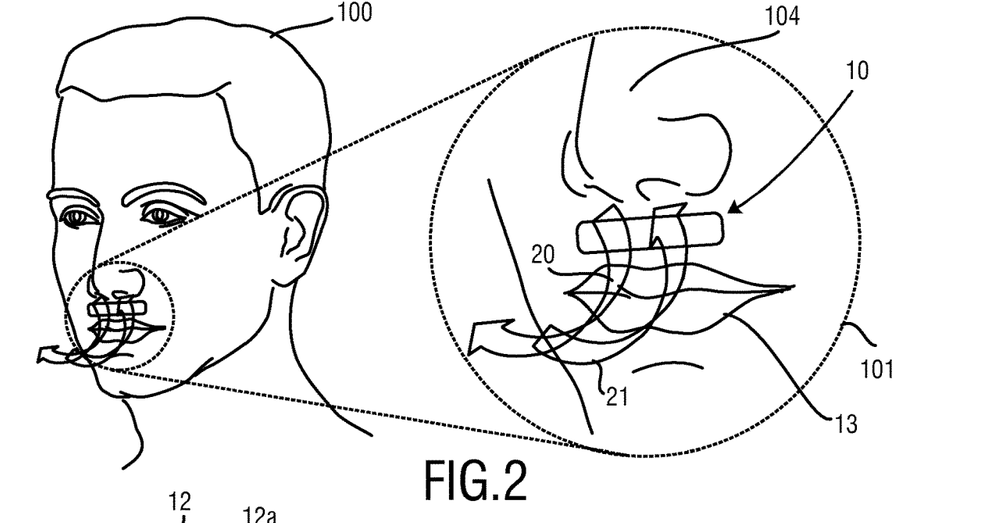
FIG. 2 shows a marker according to an aspect of the present invention applied to the subject.

FIG. 2 shows a close-up of the face of the subject 100, wherein the marker 10 is configured for application to a nasal and/or oral region 101 of the subject, in particular to a region underneath a nose 104 of the subject in the supralabial region, for example spanning across the philtrum.

In the embodiment shown in FIG. 2, the marker 10 is configured to change an optical property due to a mechanical manipulation of the marker 10 caused by a physiological process of the subject 100. An exemplary embodiment of such a marker 10 is described with reference to FIGS. 3A and 3B.

Figure 3A:
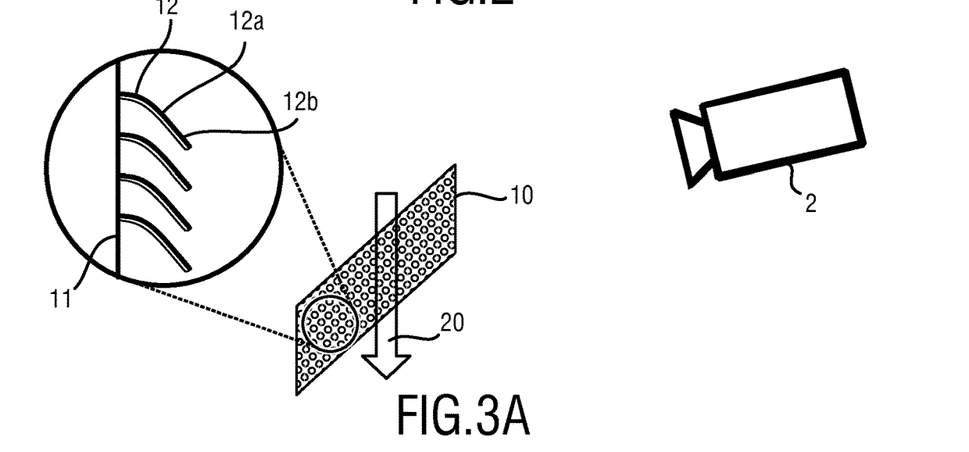
FIGS. 3A and 3B show an exemplary embodiment of a marker configured to change an optical property due to a mechanical manipulation of the marker.
Figure 3B:
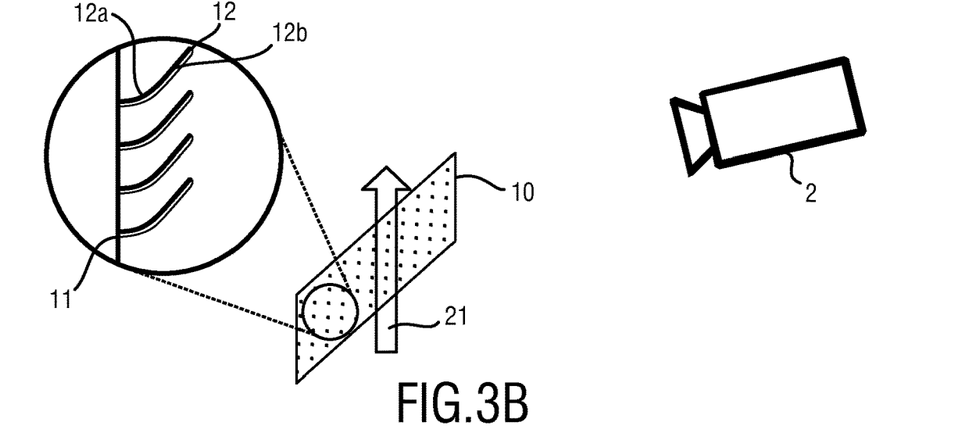

As shown in FIGS. 3A and 3B, a surface 11 of the marker 10 comprises filaments 12 protruding from said surface 11. For example these filaments are flexible filaments, in particular textile fibers that are configured to move upon a stream of air passing by. Filaments are not limited to filaments of circular cross-section but also include shapes such as, for example, a lamella structure. The inset of FIG. 3A illustrates an orientation of the filaments 12 during exhalation, wherein a flow of exhaled air 20 passes by the surface 11 of the marker during exhalation and bends the filaments 12 downwards.

In an embodiment, the filaments 12 comprise a first surface 12a having a first optical property and a second surface 12b having a second optical property. For example as shown in FIG. 3A, an upper surface 12a of the filament 12 is black, whereas a lower surface 12b is white. Alternatively, the first and second surface can have different color, different reflection or scattering properties. Advantageously the first surface 12a and the second surface 12b have a high contrast. Thus, during exhalation, the detection unit 2 sees a darker color.

The inset of FIG. 3B shows the marker 10 during inhalation, wherein a flow of air 21 passes by the marker surface 11 in an upward direction. Thereby, the filaments 12a are oriented in an upward direction, such that the white side 12b of the filament 12 is visible to the detection unit 2. Thus, during inhalation, the detection unit 2 which captures a brighter image.

In this embodiment, the analysis unit 6 is configured to evaluate the detected radiation over time and can thus to analyze the change between a darker appearance of the marker 10 as shown in FIG. 3A during exhalation and a brighter appearance of the marker 10 as shown in FIG. 3B during inhalation. Thereby, vital sign information referring to the respiration of the subject, which is invisible itself to the visible optical spectrum, gets detectable by a potentially low-cost detection unit 2.

Figure 4:
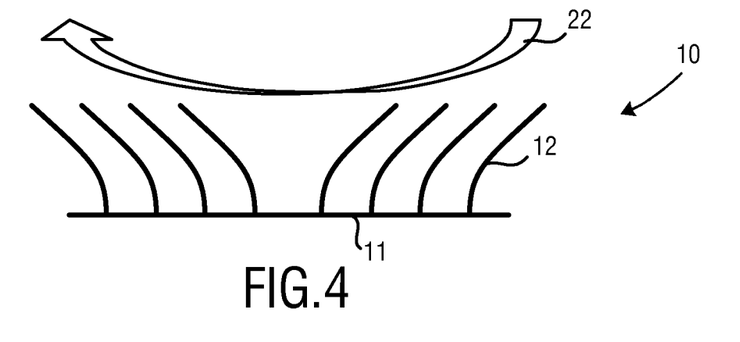
FIG. 4 shows an alternative embodiment of a marker.

In an alternative embodiment as shown in FIG. 4, a respiratory flow of air 22 does not orient all the filaments 12 of the surface 11 of the marker in the same direction but merely causes a re-orientation, wherein some filaments flex to a right and some filaments flex to a left side. It should be noted that absolute knowledge about an orientation of filaments is not mandatory, since a relative change can also be evaluated. Optionally, the period times of a first optical property and a second optical property can be compared. For example, inspiration typically has a shorter duration than expiration. Moreover, expiration is often followed by a breathing pause.

Optionally, the analysis unit 6 is configured to derive information about a tidal volume of the subject 100 with a marker as shown in FIGS. 3A and 3B. Assuming the filament is always moving back to its neutral position in case there is no airflow there are two exemplary options. As a first option, the number of filaments that move with the airflow correlates to the breathing strength. Thus, the color change contains information about the breathing strength over time. An integral of the corresponding signal over time correlates to the tidal volume. As a second option, each filament has a color/brightness scale gradient from top to the bottom. The stronger the breathing, the more of each single filament is visible to the detection unit 2. Thus, again the average color/brightness change would be indicative for the breathing strength over time. An integral of the corresponding signal over time again correlates with the tidal volume.

Referring again to FIG. 2, in an alternative embodiment, the marker is directly applied to a skin of the subject 100. For example, the marker is implemented in form of a colorimetric lipstick which is directly applied to the lips 13 of the subject. For example, the lipstick is configured to change its color or other reflectance property, in general a substance configured to change an optical property, in response to a physiological process of the subject which, for example, causes a different temperature, gas concentration or humidity at the marker. Applying the marker directly on the lips has the advantage that a breathing of the subject 100 through the mouth can also be observed.

Figure 5:
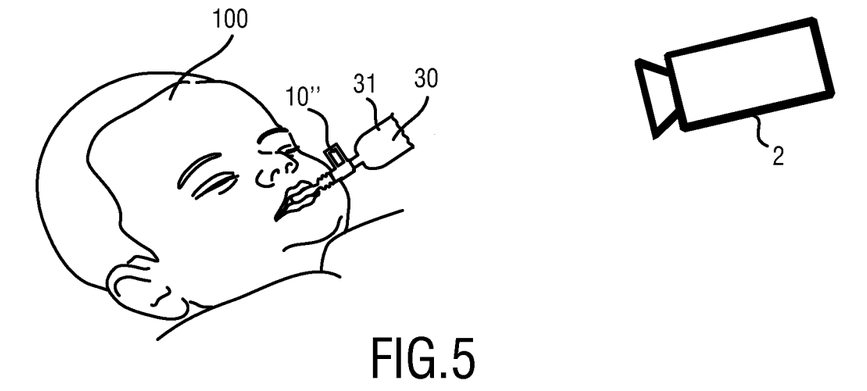
FIG. 5 shows a further embodiment of a marker.
Figure 6:
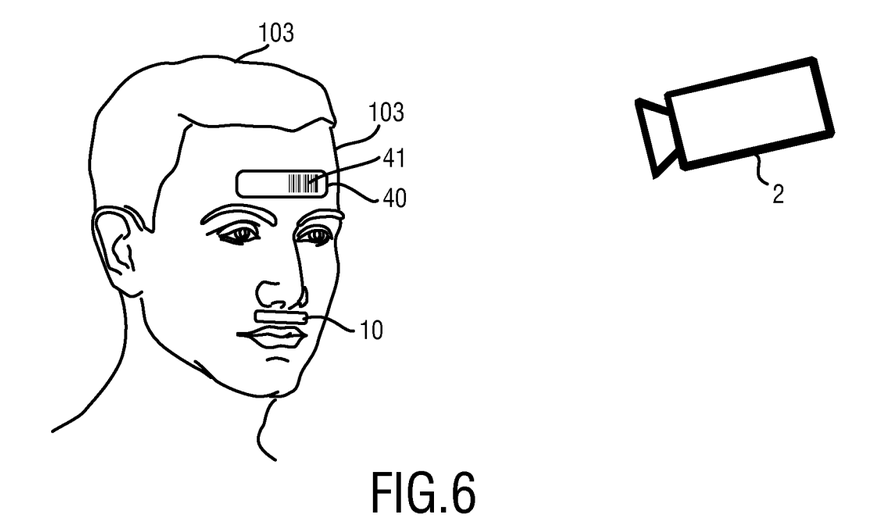
FIG. 6 shows two markers applied to a face of the subject.

Further alternative embodiments are shown with reference to FIGS. 5 and 6. In FIG. 5, the marker 10" is indirectly applied to the subject 100. The marker 10" is implemented as a part of a tubular system 30 of an intubated patient 100. In this embodiment, the marker 10" is configured to change its color due to a chemical manipulation of the marker, i.e. in response to a different carbon dioxide concentration of inhaled and exhaled air. The color change is observed with the detection unit 2 for detecting radiation from the marker and the corresponding radiation data 3 is provided to the analysis unit 6 for determining the vital sign information 7 of the subject 100 from the detected radiation by evaluating the detected radiation over time.

Optionally, besides evaluating a time-variant optical property for rate information, an actual value can be used as independent information. For example, the system 1 for determining vital sign information as disclosed herein can be combined with colorimetric and/or fluorimetric optical measurements principles known from chemical analytic sensors, for example, to determine oxygen and carbon dioxide concentrations. For determining an oxygen concentration, there are known principles of dynamic fluorescence quenching or sensors that use the fluorescence of a chemical complex in a sol-gel to measure the partial pressure of oxygen such as Joseph R. Lakowicz, "Principles of Fluorescence Spectroscopy", Third Edition, ISBN: 978-0-387-31278-1; Otto S. Wolfbeis et al., "Fiber-optic fluorosensor for oxygen and carbon dioxide" Anal. Chem., 1988, 60 (19), pp 2028-2030. For determining a carbon dioxide concentration, there are colorimetric and fluorimetric methods such as Royce N. et al., "Fluorescent-Dye-Doped Sol-Gel Sensor for Highly Sensitive Carbon Dioxide Gas Detection below Atmospheric Concentrations", Anal. Chem., 2010, 82 (2), pp 593-600; C. Malins and B. D. MacCraith, "Dye-doped organically modified silica glass for fluorescence based carbon dioxide gas detection", Analyst, 1998, 123, 2373-2376; Hiroyo Segawa et al., "Sensitivity of fiber-optic carbon dioxide sensors utilizing indicator dye", Sensors and Actuators B: Chemical, Volume 94, Issue 3, 1 Oct. 2003, Pages 276-281; Sevinc Zehra Topal et al., "A new absorption based CO2 sensor based on Schiff base doped ethyl cellulose", Turk J Chem., 36 (2012), 503-514. Using these abstract concepts for markers in the context of this invention allows remotely determining concentrations of substances in gases, tissue or body fluids. For example, the optical information, such as the actual color, may be sufficiently accurate for determining a carbon dioxide concentration of inhaled and exhaled air for certain applications. In other cases, a delta value between an inspiration phase and an expiration phase or alternatively a trend thereof can be evaluated if an absolute accuracy is not sufficient.

Exemplary parameters that can be determined include, but are not limited to exhaled carbon dioxide level, oxygen concentration (inspired and/or expired), oxygen consumption (delta between expired and inspired), oxygen uptake (efficiency indicator for lungs), temperature or temperature difference to ambient temperature, and humidity. This further includes a concentration of chemical substances, in particular chemical substances involved with certain diseases.

In order to increase the accuracy, additional reference information can be provided. For example, the marker 10" shown in FIG. 5 can be part of the tubular system 30, wherein a color of the tubular system 30 can serve as a reference surface for calibrating the system 1 for determining vital sign information, in particular for calibrating the detection unit 2 to the available light intensity and spectrum. In addition, or in the alternative, information can be encoded in the marker as shown in FIG. 6 in form of a barcode 41. The additional information can, for example, be used for calibrating the system 1, for configuring a measurement procedure or for automatically assigning the measured vital sign information to an electronic health record of the subject 100.

Alternatively, a marker can be implemented as a forehead patch 40 configured for application to the forehead 103 of the subject 100. In an embodiment, the forehead patch 40 is configured to change its color in response to a body temperature of the subject 100. In an embodiment, the forehead patch 40 is skin-colored in the visible spectral range and changes its color at non-visible wavelengths, in particular near infrared and/or near ultraviolet. An advantage of this embodiment is that the color change can still be detected by the detection unit 2 but does not significantly disturb a visual appearance.

Optionally, a plurality of markers 10, 40 can be applied to the subject 100. The markers can be configured for same or different vital signs to be measured. The detection unit 2 is configured correspondingly to detect radiation received from both markers. Furthermore, the detection unit can be configured to determine vital sign information of the subject by directly evaluating a time-variant change of the color of the skin of the subject 100.

In conclusion, the system for determining vital sign information of a subject comprising a marker for application to the subject, wherein the marker is configured to change an optical property in response to a physiological process of the subject, a detection unit for detecting radiation from the marker, and an analysis unit for determining the vital sign information of the subject from the detected radiation successfully provides a system for unobtrusive monitoring of vital signs at low system cost.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different advantages as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated. Other variations to the disclosed embodiments can be understood and effected by those skilled in the art in practicing the claimed invention, from a study of the drawings, the disclosure, and the appended claims.

The invention claimed is:

1. A system for determining breathing information of a subject comprising
    a marker configured for application to the subject, the marker including a patch with flexible filaments protruding from a surface, the filaments being configured to flex in response to air flow during inhalation and exhalation, the filaments having at least one of a color and brightness gradient along the filaments from top to bottom such that at least one of the color and brightness of the patch changes as the filaments flex,
    a camera configured to detect the changes in at least one of the color and brightness of the patch in response to the air flow, and
    a computer configured to identify the marker in a video image from the camera and determine the breathing information of the subject from the detected changes in at least one of the color and brightness of the patch.

2. The system according to claim 1, wherein the determined breathing information includes whether the subject is inhaling or exhaling.

3. The system according to claim 2, wherein the computer is further configured to determine a respiration rate of the subject and further including:
    a display device configured to display the respiration rate.

4. The system according to claim 1, wherein the filaments include:
    a first surface having a first color gradient and a second surface having a second color gradient, the first color gradient being different from the second color gradient.

5. The system according to claim 2, wherein the change in at least one of the color and brightness gradient is indicative of breathing strength over time and wherein the computer is further configured to:
    integrate the change over time to derive information about the tidal volume.

6. The system according to claim 1, wherein the patch includes a bar code or a QR code with a patient identifier detectable by the camera.

7. The system according to claim 1, wherein the marker comprises one or more optical features for detection by the camera, the one or more optical features being selected from a group of features comprising: an optical feature for tracking the marker, an optical feature for reference, an optical feature for measurement at night, and an optical feature for information coding.

8. The system according to claim 1, wherein the filaments have a color gradient from the top to the bottom.

9. A method for determining vital sign information of a subject comprising the steps of:
    applying a patch with protruding flexible filaments adjacent a nasal or oral region of the subject, the flexible filaments being configured to flex and have a first color property due to a mechanical manipulation during inhalation and a second color property during exhalation to a subject, the second color property being different from the first color property;
    detecting light reflected from the flexible filaments with a camera; and
    determining respiration information of the subject from the detected light.

10. The method according to claim 9, wherein the flexible filaments have first and second colors on first and second sides, such that patient inhalation causes the camera to see the first color and patient exhalation causes the camera to see the second color; and determining the respiration information includes:
determining a respiration rate.

11. The method according to claim 9, wherein the marker includes a bar or QR code.

12. A marker for use in a system for determining respiratory information, the marker including:

a patch configured to be applied to the subject adjacent nostrils of a subject and including filaments protruding from the surface, the filaments being configured to flex differently in response to air flow during inhalation and exhalation, wherein the filaments having a first color on a first surface and a second color on a second surface, the first color being different from the second color, the filaments being configured such that when flexing in response to inhalation, the patch shows the first color and when flexing in response to exhalation, the patch shows the second color.

13. The marker according to claim 12, wherein the filaments flex one way during inhalation and an opposite way during exhalation.

14. The marker according to claim 13, wherein the filaments have color gradients from top to bottom to provide an indication of breathing strength.

15. The marker according to claim 13, wherein the patch includes a bar or QR code carrying information about the patient.

16. The marker according to claim 13, further including a second patch configured to be applied to the subject in a reference location insensitive to exhalation or inhalation.

17. A marker for use in a system for determining respiratory information, comprising:

a lipstick configured to be applied to the lips of a subject, the lipstick being configured to have a first color property when the subject inhales and a second color property when the subject exhales, the second color property being different from the first color property.

18. A method of determining respiratory information of a patient, the method comprising:

applying a colorimetric lipstick to lips of the patient, the colorimetric lipstick being configured to have different optical properties during inhalation than during exhalation;

with a camera, detecting light reflected from the colorimetric lipstick and generating an output signal indicative of changing of the optical properties as the patient breathes; and converting the output signal into the respiratory information.

19. The method according to claim 18, wherein the respiratory information includes respiration motion.

* * * * *